United States Patent
Tesson et al.

(10) Patent No.: US 10,745,373 B2
(45) Date of Patent: Aug. 18, 2020

(54) PROCESS FOR PREPARING FLUORESCEIN QUINOID FORM

(71) Applicant: Delmar Chemicals Inc., LaSalle (CA)

(72) Inventors: Nicolas Tesson, Bacelona (ES); Eduard Bugan, LaSalle (CA); Nadejda Spassova, LaSalle (CA); Alain Menard, LaSalle (CA)

(73) Assignee: Delmar Chemicals Inc., LaSalle (CA)

( * ) Notice: Subject to any disclaimer, the term of this patent is extended or adjusted under 35 U.S.C. 154(b) by 0 days.

(21) Appl. No.: 16/528,096

(22) Filed: Jul. 31, 2019

(65) Prior Publication Data

US 2020/0039949 A1    Feb. 6, 2020

(30) Foreign Application Priority Data

Aug. 1, 2018    (EP) ..................... 18186849

(51) Int. Cl.
  *C07D 311/82*    (2006.01)
(52) U.S. Cl.
  CPC ........ *C07D 311/82* (2013.01); *C07B 2200/13* (2013.01)
(58) Field of Classification Search
  CPC ............. C07D 311/82; C07B 2200/13
  USPC ........................................... 549/391
  See application file for complete search history.

(56) References Cited

FOREIGN PATENT DOCUMENTS

JP        2017095453    *  6/2017
WO    WO-2017082430 A1    5/2017

OTHER PUBLICATIONS

Berge et al, Pharmaceutical Salts, Journal of Pharmaceutical Sciences, Jan. 1977, vol. 66, No. 1, p. 1-19 (Year: 1977).*
Tremayne, M., et al., "Structure Determination of a Complex Organic Solid from X-ray Powder Diffraction Data by a Generalized Monte Carlo Method: The Crystal Structure of Red Fluorescein," Angew. Chem. Int. Ed. Engl. 36(7):770-772, Wiley Online Library, United States (1997).
Arhangelskis, M., et al. "Rationalization of the Color Properties of Fluorescein in the Solid State: A Combined Computational and Experimental Study," Chem. Eur. J., 22:10065-10073, Wiley-VCH, German (2016).

* cited by examiner

*Primary Examiner* — Taylor V Oh
(74) *Attorney, Agent, or Firm* — Sterne, Kessler, Goldstein Fox; Olga Partington (57) ABSTRACT

The present invention relates to a process for preparing fluorescein quinoid form of Formula (I):

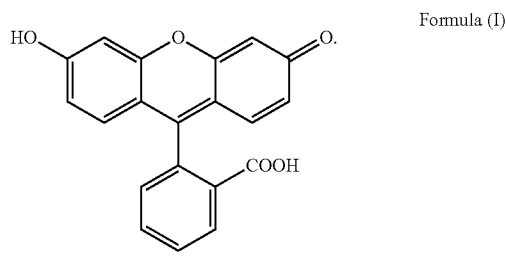

Furthermore, the present invention relates to a new solid fluorescein form and a process for the preparation thereof. The present invention also relates to the use of said new solid fluorescein form in the synthesis of fluorescein quinoid form.

15 Claims, 5 Drawing Sheets

Figura 5A

Figura 5B

PROCESS FOR PREPARING FLUORESCEIN QUINOID FORM

This patent application claims priority to and benefit of EP Application No. EP18186849, filed on Aug. 1, 2018.

TECHNICAL FIELD OF THE INVENTION

The present invention relates to a process for preparing fluorescein quinoid form (abbreviated Fls Q) of Formula (I):

Formula (I)

Furthermore, the present invention relates to a new solid fluorescein form and a process for the preparation thereof. The present invention also relates to the use of said new solid fluorescein form in the synthesis of fluorescein quinoid form.

BACKGROUND OF THE INVENTION

Fluorescein (abbreviated Fls) is a manufactured organic compound and a dye which is widely used as fluorescent tracer for many applications. Fls exists in several tautomeric forms and in some solid forms.

Among the various crystalline form disclosed in the prior art, particular reference is made to specific solvated and not solvated forms. In particular, Fls Q known as quinoid form (which is a not solvated form, also called red form; also characterized in *Angew., Chem. Int Ed Engl.*, 1997, 36(7), 770-772) has the following formula (I):

Formula (I)-Fls Q

Fls Z form, known as zwitterionic form (which is a not solvated form, also called yellow form; see *Chem. Eur. J.* 2016, 22, 2-20, has the following formula:

Fls Z

Fls L form, known as lactone form, has the following formula:

Fls L

FlsL, at present, is known only as a solvated form.

WO 2017/082430 discloses a method for the purification of fluorescein sodium by crystallizing fluorescein sodium with 2-propanol or 2-butanol.

SUMMARY OF THE INVENTION

Therefore, the problem addressed by the present invention is to provide a process capable of enhancing the filtration behaviour of Fls Q form, as well as improving the purity degree of the final obtained Fls Q form.

This problem is solved by a specific preparation process of Fls Q involving the formation of a specific fluorescein solid form.

Further characteristics and advantages of the preparation process and the specific fluorescein solid form according to the invention will become apparent from the below-reported description of preferred embodiments, given by way of a non-limiting example.

DETAILED DESCRIPTION OF THE INVENTION

According to a first aspect, the present invention relates to process for preparing fluorescein quinoid form (Fls Q) of Formula (I):

Formula (I)

comprising the steps of:
a) preparing fluorescein mesylate salt or co-crystal;
b) converting the fluorescein mesylate salt or co-crystal into fluorescein quinoid form of formula (I) by treatment with water or a mixture of water and a water-soluble organic solvent.

Advantageously, the Applicant has surprisingly found that through the process of the present invention, wherein said process involves the preparation of a fluorescein mesylate salt or co-crystal (abbreviated Fls A) then converted into fluorescein quinoid form (FLs Q), it is possible to obtain an enhanced filtration of Fls Q, and in particular, to avoid filtration problems, especially at industrial scale.

As further advantage, the fluorescein quinoid form (FLs Q) has an improved purity degree.

The fluorescein mesylate salt or co-crystal prepared in step a), can have the following formulae (IIa) and (IIb), respectively:

(IIa)

(IIb)

The preparation of fluorescein mesylate salt or co-crystal of step a) can be carried out by converting fluorescein, in particular fluorescein quinoid form (Fls Q), into fluorescein mesylate salt in the presence of methane sulfonic acid (MsOH) or reacting resorcinol and phthalic anhydride in methane sulfonic acid. Preferably, the fluorescein mesylate salt or co-crystal of step a) is in an isolated form. The term isolated form means a solid, wet or dry, which is separated by the solvent.

According to a preferred embodiment, the fluorescein mesylate salt or co-crystal has a DSC onset at a value of 285±1° C. and/or a DSC peak of 289±1° C.

According to another preferred aspect, the fluorescein mesylate salt or co-crystal has a characteristic X-ray powder diffraction pattern with at least one characteristic peak expressed in 2-Theta values (2θ) at 8.3±0.2, 15.0±0.2, 24.1±0.2, 28.6±0.2. Preferably, the fluorescein mesylate salt or co-crystal has a characteristic X-ray powder diffraction pattern consisting of a characteristic peak expressed in 2-Theta values (2θ) at 8.3±0.2, 15.0±0.2, 24.1±0.2, 28.6±0.2.

According to another preferred aspect, the fluorescein mesylate salt or co-crystal further has a characteristic X-ray powder diffraction pattern with at least one characteristic peak expressed in 2-Theta values (2θ) at 10.7±0.2, 11.9±0.2, 13.4±0.2, 16.8±0.2, 26.5±0.2, 27.8±0.2.

The fluorescein mesylate salt or co-crystal has a molar ratio of 1:1 between fluorescein and methane sulfonic acid.

According to a preferred embodiment, the above-mentioned process further comprises a step a'), which follows step a) and preceeded step b), of removing possible free methane sulfonic acid (abbreviated MsOH) from the fluorescein mesylate salt or co-crystal prepared in step a) through a washing with water or a mixture of water and a water-soluble organic solvent. Preferably, the removal of possible free methane sulfonic acid is carried out by washing or slurring, for example by washing with or slurring into a solvent, such as water, $C_1$-$C_3$ alcohol or a mixtures thereof. Alternatively, the removal of possible free methane sulfonic acid can be carried out by recrystallization, for example by pH-change mediated crystallization. As intended herein, the term free methane sulfonic acid (MSA) means MSA which is not part of the methane sulfonic acid salt or co-crystal, but which is an impurity thereof.

As intended herein, the expression $C_1$-$C_3$ alcohol means methanol (MetOH), ethanol (EtOH), iso-propanol, n-propanol, respectively.

Without being bound to any theories, experimental evidences suggests that the fluorescein mesylate salt or co-crystal converts into Fls Q in the absence of methane sulfonic acid, said conversion being reversible. Therefore, the above-mentioned step a') is particularly advantageous in order to avoid the presence of methane sulfonic acid residues, which could prevent the complete conversion of the fluorescein mesylate salt or co-crystal into Fls Q form (see experimental evidences in example 6). The incomplete conversion of Fls A into Fls Q gives serious filtration problems.

According to a preferred embodiment, when in step b) a mixture of water and a water-soluble organic solvent is used, the water-soluble organic solvent is a $C_1$-$C_3$ alkyl alcohol, preferably methanol or ethanol, even more preferably ethanol.

As intended herein, the term volumes means volume of solvent per unit of product, thus, for example, 1 volume is 1 Liter per 1 Kilo, or 1 mL for 1 gram, or 1 microliter per 1 milligram. Thus, 10 volumes means for example 10 liters per 1 Kilogram of substance. With reference to the above-mentioned mixture of water and a water-soluble organic solvent, the water and water-soluble organic solvent used in the mixture used in step b).

The volumes of each water soluble solvent and water used in the mixture of solvent and water used in step b) range preferably from 1 to 10 volumes, more preferably from 2 to 7 volumes, more preferably from 3 to 5 volumes.

Furthermore, when in the step b) a mixture of water and a water-soluble organic solvent is used, the water-soluble organic solvent can be added after or before a treatment with water, preferably after since the conversion is faster. Alternatively, water and the water-soluble organic solvent can be added simultaneously or as a mixture thereof.

According to a preferred embodiment, the treatment with water or a mixture of water and a water-soluble organic solvent of step b) is carried out at a temperature from 20° C. to 60° C., preferably from 30° C. to 50° C., even more preferably from 35 to 45° C. According to a particularly preferred embodiment, said temperature is of about 40° C.

According to a preferred embodiment, the treatment with water or a mixture of water and a water-soluble organic solvent of step b) is carried out for a period of time from 10 min to 20 h, preferably from 15 min to 10 h, more preferably from 20 min to 5 h, even more preferably from 30 min to 2 h. According to a particularly preferred embodiment, said period of time is from 15 min to 2 h.

According to a particularly preferred embodiment, the treatment with water or a mixture of water and a water-soluble organic solvent of step b) is carried out for a period of time from 15 min to 2 h and at a temperature from 35 to 45° C.

However, it is generally expected that the more is the amount of water in the mixture of water and a water-soluble organic solvent of step b) the less is the period of time and the temperature value to complete the conversion of step b).

Thus, for instance, when there is only water, the conversion of step (b) lasts only 20 min at 40° C.

As far as the particle size distribution (PSD) is concerned, the fluorescein quinoid form has a PSD having a d(0.9) comprised in the range from 30 to 100 μm.

A further aspect is a fluorescein mesylate salt or co-crystal. Some of the possible forms and/or characteristics of said fluorescein mesylate salt or co-crystal are as defined above.

A further aspect is a synthesis process of fluorescein mesylate salt or co-crystal comprising a step of treating fluorescein of formula (I) with methane sulfonic acid, in particular fluorescein quinoid form.

A further aspect is a process for removing possible free methane sulfonic acid from the fluorescein mesylate salt or co-crystal prepared in step a) as defined above through a washing with water or a mixture of water and a water-soluble organic solvent.

Preferably, the amount of possible free methane sulfonic acid from the fluorescein mesylate salt or co-crystal to be removed ranges from 0.1 to 10% weight as referred to the total % weight of the fluorescein mesylate salt or co-crystal.

A further aspect is a process for the purification of fluorescein quinoid form (Fls Q) from fluorescein mesylate salt or co-crystal impurity to be carried out by treatment of Fls Q with water or a mixture of water and a water-soluble organic solvent. Such water-soluble organic solvent being as defined above.

Advantageously, said purification step of fluorescein quinoid form from a fluorescein mesylate salt or co-crystal (abbreviated Fls A) is important since Fls Q can contain fluorescein mesylate salt or co-crystal as impurity, therefore such purification is useful in order to remove said impurity. Moreover, it favourites fast filtrations of Fls Q. Indeed, the presence of Fls A as impurity of Fls Q gives serious filtration problems of the suspension of Fls Q. Said treatment of Fls Q could advantageously be applied also to Fls Q prepared according to the process of the invention, for instance as further step after step b) if step b) is incomplete, i.e. if it provides Fls Q containing Fls A as impurity.

A further aspect is the use of a fluorescein mesylate salt or co-crystal for synthesizing fluorescein quinoid form (FLs Q) of Formula (I):

Formula (I)

EXPERIMENTAL SECTION

All the raw materials are commercially available, for example by Sigma-Aldrich.

Example 1

Preparation of Fluorescein Mesylate Salt or Co-Crystal

Figure 1A:
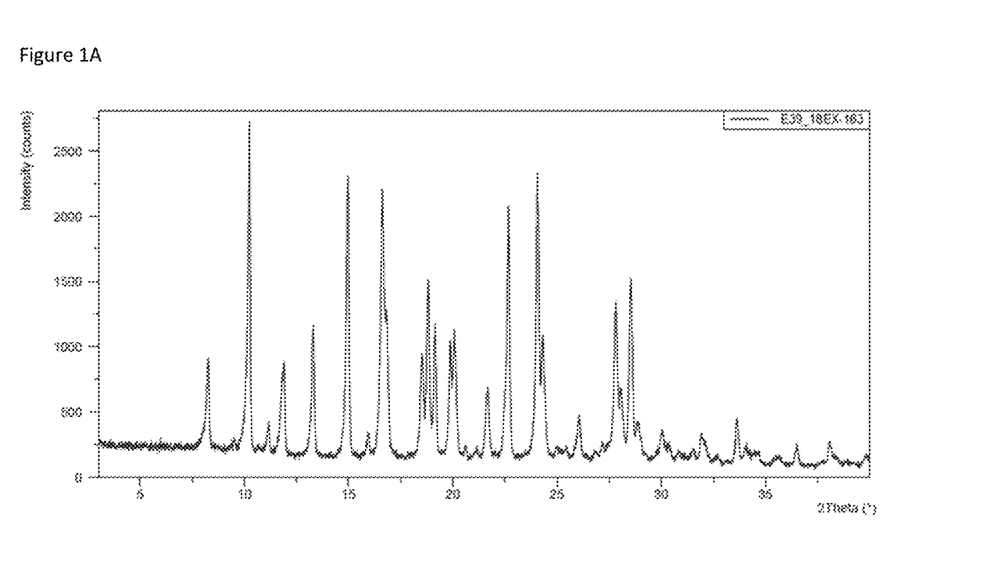
FIGS. 1A and 1B show the XPRD diffractogram of fluorescein mesylate salt or co-crystal (abbreviated Fls A).
Figure 1B:
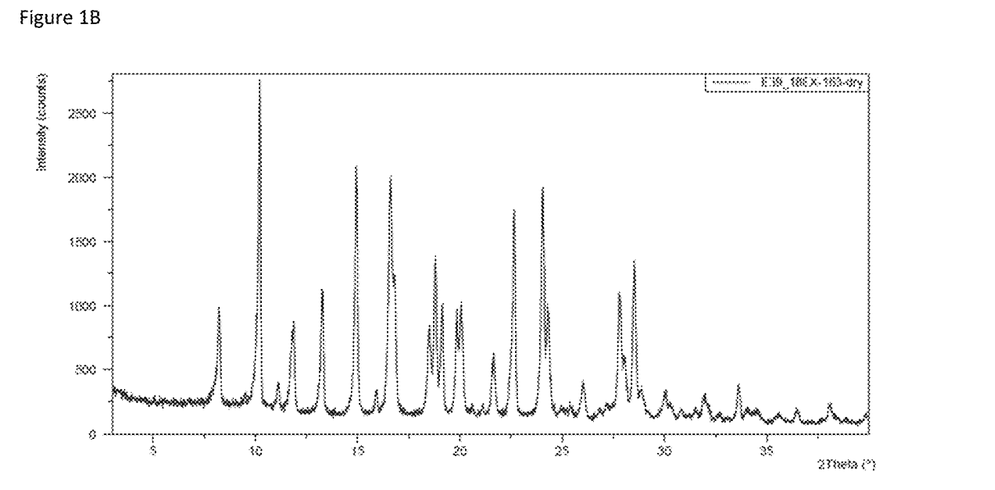

A 2 L 4-neck RBF was charged with resorcinol (148.7 g) and phthalic anhydride (100 g) and methane sulfonic acid (740 g) and the mixture was heated at a temperature of about 82° C. The mixture was stirred at 80-85° C. for 4 hours. After cooling to 10° C., the mixture was left under stirring until the precipitation of the product and was subsequently quenched over 1000 ml of water (22.5° C.) maintaining, during the addition, a temperature between 35 and 45° C. Then, a filtration under vacuum was carried out. The wet cake contained the fluorescein mesylate salt or co-crystal (herein after called Fls A) was washed twice with 2×150 ml of water. A sample of wet cake was retained (named LA-1-09) for further experiments. The wet cake was stable after drying under vacuum (both at room temperature and at 45° C.). Furthermore, XPRD diffractogram of Fls A as wet sample is reported in FIG. 1A and the corresponding data are also reported in the following table 1 (wet fluorescein mesylate salt peak list). The XPRD diffractogram of Fls A as dry sample is reported in FIG. 1 B. It was also worth noted that significant differences were not observed between wet and dried Fls A.

TABLE 1

| Angle (2-Θ° ± 0.1) | Intensity (%) |
|---|---|
| 8.3 | 28 |
| 10.3 | 100 |
| 11.2 | 8 |
| 11.8 | 24 |
| 11.9 | 25 |
| 13.3 | 40 |
| 15.0 | 85 |
| 16.0 | 6 |
| 16.6 | 82 |
| 16.9 | 40 |
| 18.5 | 31 |
| 18.8 | 49 |
| 19.2 | 38 |
| 19.9 | 35 |
| 20.1 | 37 |
| 20.6 | 3 |
| 21.1 | 2 |

TABLE 1-continued

| Angle (2-Θ° ± 0.1) | Intensity (%) |
|---|---|
| 21.7 | 21 |
| 22.7 | 78 |
| 24.1 | 87 |
| 24.3 | 38 |
| 25.0 | 2 |
| 25.5 | 2 |
| 26.1 | 12 |
| 27.2 | 4 |
| 27.8 | 45 |
| 28.1 | 20 |
| 28.6 | 53 |
| 28.9 | 11 |
| 30.1 | 8 |
| 30.4 | 4 |
| 31.5 | 3 |
| 31.9 | 8 |
| 32.7 | 2 |
| 33.6 | 13 |
| 34.1 | 4 |
| 34.6 | 3 |
| 35.6 | 2 |
| 36.5 | 5 |
| 38.1 | 6 |

Figure 3A:
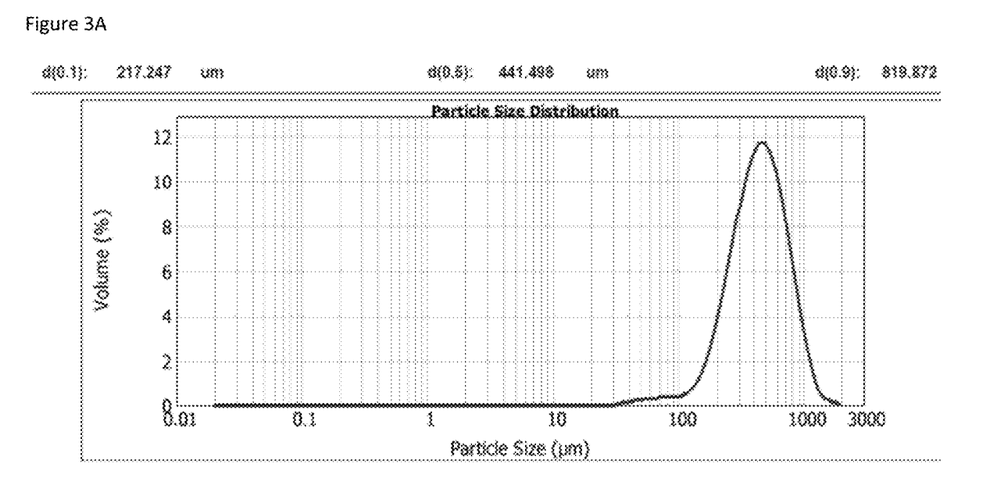
FIGS. 3A and 3B show the PSD (particle size distribution) of Fls A and Fls Q, respectively.

Another characterization was carried out about the particle size distribution (PSD) of Fls A. As shown in FIG. 3A, the PSD analysis indicated a dispersion essentially monomodal with big aggregates around 500 μm.

Example 2

DSC Analysis

Figure 4:
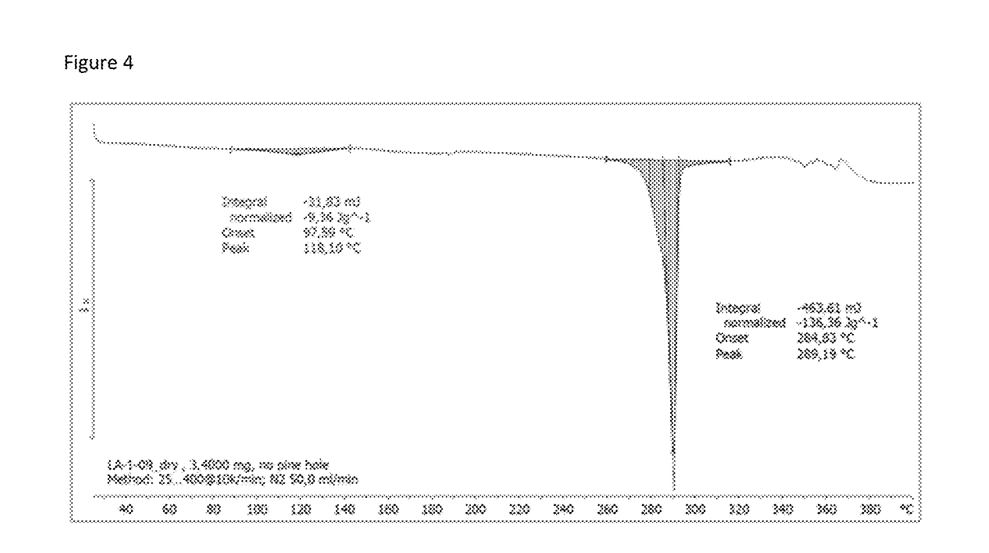
FIG. 4 shows the DSC of Fls A.
Figure 5A:
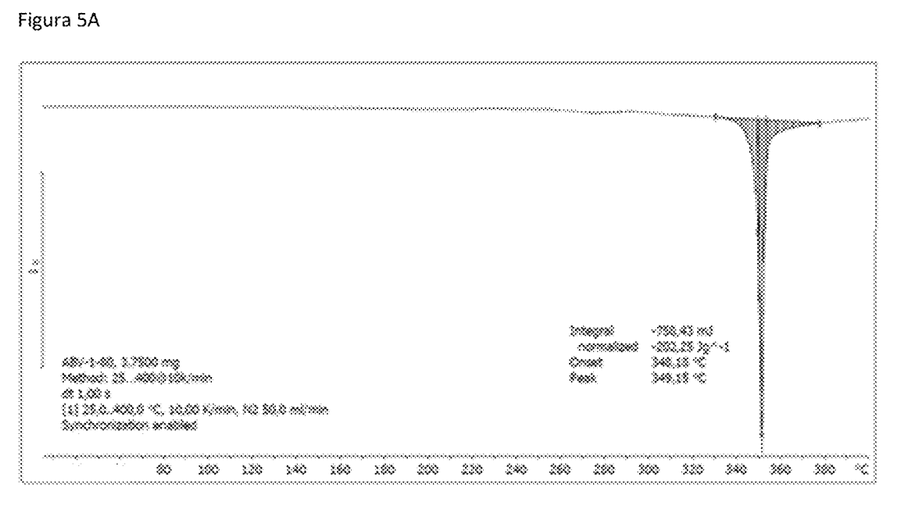
FIGS. 5A and 5B shows the DSC of Fls Q.
Figure 5B:
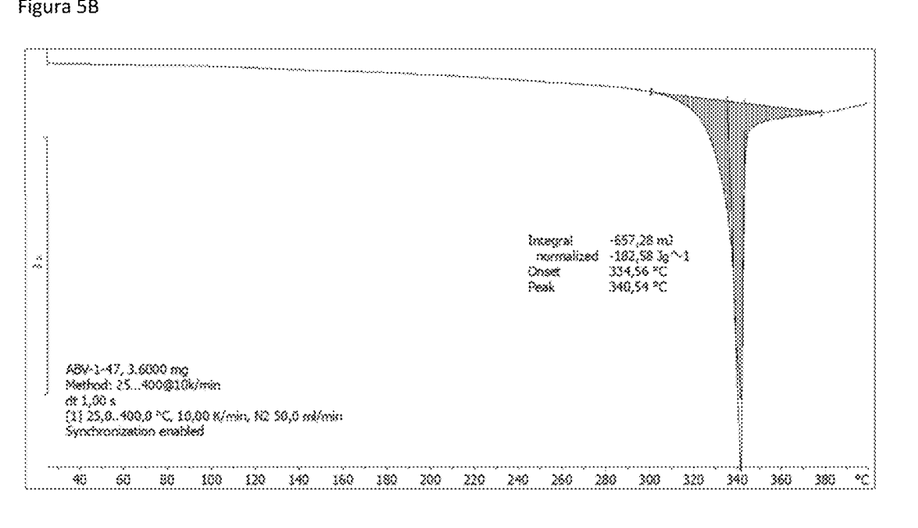

DSC analyses were recorded with a Mettler Toledo DSC2. The samples were weighed into a 40 μL aluminium crucible with or without a pinhole (depending on the sample characteristics) and heated from 25 to 400° C. at a rate of 10° C./min, under nitrogen (50 mL/min). The resulting DSC for Fls A and Fls Q are reported in FIGS. 4 and 5A and 5B, respectively.

Example 3

XPRD Method

Diffraction measurements were performed at ambient conditions on a PANalytical X'Pert PRO Θ-Θ diffractometer of 240 mm of radius in reflection geometry, equipped with Cu Kα radiation and a PIXcel detector, operated at 45 kV and 40 mA. Each sample was mounted on a zero-background silicon holder and allowed to spin at 0.25 rev/s during the data collection. The measurement angular range was 3.0-40.0° (2Θ) with a step size of 0.013°. The scanning speed was 0.082°/s (40.80 s/step). The XPRD of Fls A (on a wet sample and a dry sample).

Example 4

Conversion from Fls A to Fls Q

Figure 2:
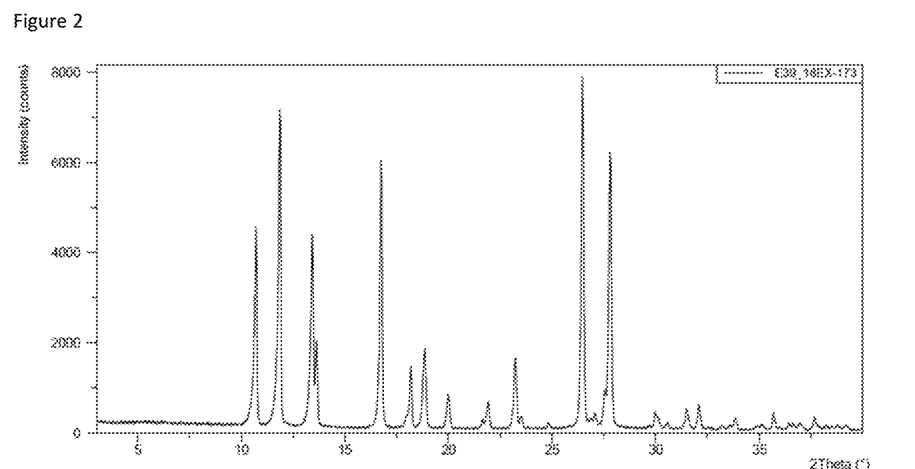
FIG. 2 shows the XPRD diffractogram of Fls Q.

Fls A recovered after the quench in water and filtration was treated (by trituration) with a mixture of EtOH/water (1:1 ca. 5 V) 1 h at 40° C. and a conversion into Fls Q was observed. The suspension was filtered and the product dried. The XPRD diffractogram of Fls Q are also reported in the following table 2 and in FIG. 2.

TABLE 2

| Angle (2-Θ° ± 0.1) | Intensity (%) |
|---|---|
| 10.7 | 52 |
| 11.3 | 1 |
| 11.9 | 88 |
| 13.4 | 52 |
| 13.7 | 24 |
| 16.8 | 74 |
| 18.2 | 15 |
| 18.8 | 19 |
| 18.9 | 22 |
| 20.0 | 10 |
| 21.6 | 2 |
| 21.9 | 7 |
| 23.3 | 20 |
| 23.5 | 3 |
| 24.8 | 1 |
| 26.5 | 100 |
| 27.1 | 3 |
| 27.5 | 9 |
| 27.8 | 78 |
| 30.0 | 4 |
| 30.6 | 2 |
| 31.5 | 5 |
| 32.1 | 6 |
| 33.2 | 1 |
| 33.8 | 3 |
| 35.1 | 1 |
| 35.7 | 4 |
| 36.4 | 1 |
| 36.6 | 1 |
| 37.0 | 1 |
| 37.7 | 3 |
| 38.3 | 1 |
| 38.7 | 1 |

Figure 3B:
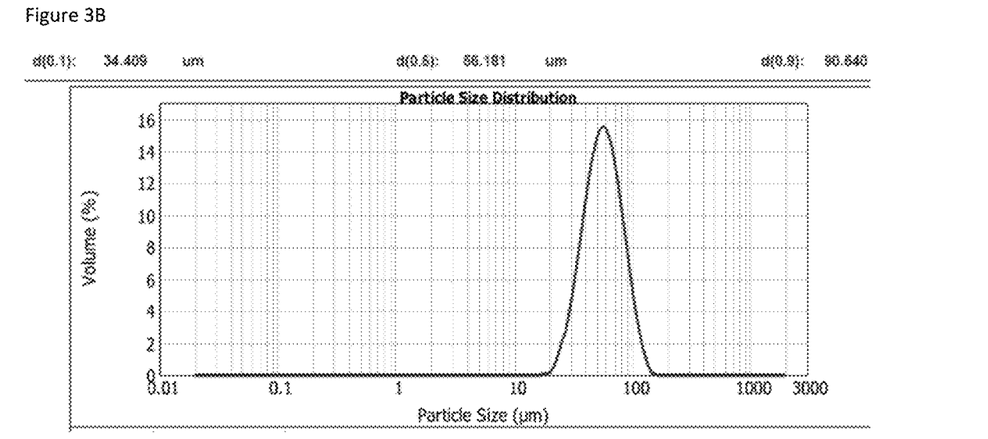

Furthermore, PSD analysis for Fls Q was carried out. As shown in FIG. 3B, the PSD analysis indicated a narrow monomodal dispersion with a particle size d(50) about 60 μm and/or d(90) about 90 μm.

Example 5

Filtration Performance of Fls Q

Slurrying experiments were performed starting from the wet-cake LA-1-09 (Fls A, crude before the treatment with water or water/ethanol mixture) at 1 g scale. After drying to constant weight under vacuum at RT and then at 40° C., it was determined that the wet crude sample LA-1-09 (Fls A) contained ca. 20% of volatile solvents (ca. 80% w/w recovered after drying). Therefore, dry LA-1-09 was slurried in ca. 4 V of the selected solvents or solvent mixtures at 40° C. After the experiments, the filtration behavior was checked and the resulting solids were analyzed by XRPD without drying.

TABLE 3

| Entry | Experiments | Solvent(s) | Time | Filtration | XPRD |
|---|---|---|---|---|---|
| 1 | E39-22-005B | EtOH [4 V] | 1 h | Good | Fls A |
| 2 | E39-22-005A | H2O [4 V] | 1 h | | Fls Q |
| 3 | E39-22-009B | EtOH [2 V], then +H2O [2 V] | 1 h + 1 h | | Fls A, then Q |
| 4 | E39-22-009A | H2O [2 V], then +EtOH [2 V] | 1 h + 1 h | | Fls Q + Fls A min, then Fls Q |

In view of the above data shown in table 3, the conversion of FLs A into Fls Q during the treatment step of step b) is due to the presence of water:

Fls A remained stable in EtOH (entry 1); i.e. no conversion to Fls Q.

Fls A converted into Fls Q in water (4 V) after ca. 20 min according to XRPD analysis (entry 2);

Fls A converted partially into Fls Q in a lower amount of water (2 V instead of 4 V) (entry 4).

Regardless of the addition order of the solvents, final mixtures of water/EtOH (1:1) afforded a complete conversion of Fls A into Fls Q after 1+1 h (i.e. 2 h) slurring at 40° C. (entries 3 and 4).

The filtration of the recovered solids was good in all cases. Therefore, the solvent proportion or the solvent addition order seems not to affect the filtration behavior.

Further experiments was carried out in order to investigate in more detail further embodiments and data are reported in the following table 4.

TABLE 4

| Entry | Experiments | Fls A Starting material | Water treatment | Scale | Slurrying conditions | T (° C.) | Time | Filtration | XPRD |
|---|---|---|---|---|---|---|---|---|---|
| 5 | E39-22-018 (blank) | — | Without water washing Drying at RT under vaccum | — | EtOH/H2O 1:1 [5 V] | 40 | 1 h | Good | Fls Q |
| 6 | E39-22-017 | — | Water washing (3 × 1 V) 1.24 V of residual water | — | EtOH/H2O 1:1 [5 V] | | 1 h | | Fls Q |
| 7 | E39-22-021 (1 g) | Water washing (3 × 1 V) + drying at RT under vaccum | — | — | H2O [5 V] | | 1 h | | Fls Q |
| 8 | E39-22-023 (1 g) | | — | — | H2O [2.5 V], then + EtOH [2.5 V] | | 1 h + 1 h | | Fls Q |
| 9 | E39-22-31 (1 g) | Recrystallyzed in MsOH/water from crude Fls Q | — | — | H2O [2.5 V], then + EtOH [2.5 V] | | 1 h + 1 h | Average | Fls Q |
| 10 | E39-22-023 (1 g) | | Water washing (3 × 1 V) + drying at RT under vaccum | 1 g | H2O [2.5 V] Then + EtOH [2.5 V] | | 1 h + 1 h | Good | Fls Q |
| 11 | E39-22-035 (50 g) | | | 49 g | H2O [2.5 V] then + EtOH [2.5 V] | | 1 h | | |

Example 6

Influence of Residual MsOH in Fls A on the Conversion of Fls A into Fls Q

Slurrying experiments were performed from the wet-cake LA-1-09 (Fls A) at 1 g scale. LA-1-09 was slurried in ca. 4 V of EtOH/water 1:1 at 40° C. with different amount of added MsOH (see table 5 below).

TABLE 5

| Entry | Experiments | Solvent(s) | Time | Filtration | XPRD |
|---|---|---|---|---|---|
| 1 | E39-22-008B | EtOH/water 1:1 [4 V] + 0.1 eq. MsOH | 1 h | Good | Fls Q |
| 2 | E39-22-008A | EtOH/water 1:1 [4 V] + 0.5 eq. MsOH | | Good | Fls A + Fls Q traces |
| 3 | E39-22-008B | EtOH/water 1:1 [4 V] + 1 eq. MsOH | | Slow | |

In view of data shown in table 5, it can be observed how Fls A remained stable in the presence of an excess of MsOH (higher than 0.1 eq.): Fls A+Fls Q traces were observed by XRPD (entries 2 and 3). As the presence of MsOH excess seems to stabilize Fls A, the conversion of Fls A into Fls Q tends to be inhibited or more difficult to occur.

Furthermore, the filtration of the solid Fls Q was good except when the slurrying in EtOH/water was performed with a large excess of MsOH (entry 3). However, the conversion of Fls A into Fls Q is not complete in this case.

Thus, when Fls A contains large amounts of residual methane sulfonic acid, as an impurity, the treatment of step a') with water or a mixture of water and a water-soluble organic solvent is suggested and preferred.

The invention claimed is:

1. A process for preparing a fluorescein quinoid form of Formula (I):

Formula (I)

comprising the steps of:
a) preparing a mesylate salt of fluorescein or a methanesulfonic acid-fluorescein co-crystal by converting fluorescein in the presence of methane sulfonic acid into the salt or the co-crystal, or by reacting resorcinol and phthalic anhydride in methane sulfonic acid;
b) converting the salt or the co-crystal into the fluorescein quinoid form of formula (I) by treating the salt or the co-crystal with water or a mixture of water and a water-soluble organic solvent.

2. The process according to claim 1, wherein the water-soluble organic solvent is a $C_1$-$C_3$ alkyl alcohol.

3. The process according to claim 2, wherein the $C_1$-$C_3$ alkyl alcohol is methanol or ethanol.

4. The process according to claim 1, wherein the fluorescein quinoid form has a particle size distribution having a d(0.9) from 30 to 100 μm.

5. The process according to claim 1, wherein when a mixture of water and a water-soluble organic solvent is used in step b), the water-soluble organic solvent is added after or before a treatment with water.

6. The process according to claim 1, wherein the molar ratio of fluorescein to mesylate in the salt or fluorescein to methanesulfonic acid in the co-crystal is 1:1.

7. The process according to claim 1, wherein the salt or the co-crystal has a DSC onset value of 285±1° C. and a DSC peak of 289±1° C.

8. The process according to claim 1, wherein the salt or the co-crystal is characterized by an X-ray powder diffraction pattern having peaks at 8.3±0.2, 15.0±0.2, 24.1±0.2, and 28.6±0.2 degrees two theta (2θ).

9. The process according to claim 1, further comprising a step of isolating the salt or the co-crystal.

10. The process according to claim 1 further comprising removing free methane sulfonic acid from the mesylate salt of fluorescein or the methanesulfonic acid-fluorescein co-crystal prepared in step a) through washing the salt or the co-crystal with water or a mixture of water and a water-soluble organic solvent.

11. A salt or a co-crystal, wherein said salt or the co-crystal is characterized by one or more of a)-e):
   a) a molar ratio of fluorescein to mesylate in the salt or fluorescein to methanesulfonic acid in the co-crystal is 1:1;
   b) a DSC onset value of 285±1° C.;
   c) a DSC peak of 289±1° C.;
   d) an X-ray powder diffraction pattern having peaks at 8.3±0.2, 15.0±0.2, 24.1±0.2, and 28.6±0.2 degrees two theta; or
   e) the salt or the co-crystal is isolated.

12. A process for purifying fluorescein quinoid form of Formula (I) from an impurity:

Formula (I)

comprising treating the mesylate salt of fluorescein or the methane sulfonic acid-fluorescein co-crystal with water or a mixture of water and a water-soluble organic solvent, thereby removing the impurity.

13. A process for synthesizing fluorescein quinoid form of Formula (I):

(I)

comprising converting a mesylate salt of fluorescein or a methanesulfonic acid-fluorescein co-crystal into the fluorescein quinoid form of Formula (I) by treating the salt or the co-crystal with water or a mixture of water and a water-soluble organic solvent.

14. The process according to claim 1, wherein the salt or the co-crystal has a DSC onset value of 285±1° C.

15. The process according to claim 1, wherein the salt or the co-crystal has a DSC peak of 289±1° C.

* * * * *